US009063071B2

(12) United States Patent
Iwamoto et al.

(10) Patent No.: US 9,063,071 B2
(45) Date of Patent: Jun. 23, 2015

(54) MULTI-ION SENSOR (71) Applicant: HORIBA, Ltd., Kyoto-shi, Kyoto (JP)

(72) Inventors: Yasukazu Iwamoto, Kyoto (JP); Hiromi Ohkawa, Kyoto (JP)

(73) Assignee: HORIBA, LTD. (JP)

( * ) Notice: Subject to any disclaimer, the term of this patent is extended or adjusted under 35 U.S.C. 154(b) by 0 days.

(21) Appl. No.: 14/052,228

(22) Filed: Oct. 11, 2013

(65) Prior Publication Data

US 2014/0105788 A1  Apr. 17, 2014

(30) Foreign Application Priority Data

Oct. 11, 2012 (JP) ................. 2012-226286

(51) Int. Cl.
| | |
|---|---|
| *G01N 27/27* | (2006.01) |
| *G01N 27/403* | (2006.01) |
| *G01N 27/30* | (2006.01) |
| *G01N 27/333* | (2006.01) |
| *G01N 33/49* | (2006.01) |
| *G01N 27/327* | (2006.01) |

(52) U.S. Cl.
CPC ............ *G01N 27/27* (2013.01); *G01N 27/4035* (2013.01); *G01N 27/307* (2013.01); *G01N 27/333* (2013.01); *G01N 33/492* (2013.01); *G01N 27/3272* (2013.01)

(58) Field of Classification Search
CPC ............. G01N 27/333; G01N 27/414; G01N 27/4035; G01N 27/0031; G01N 27/492; G01N 27/84; G01N 2410/10; B01L 2300/064
USPC ................................. 204/416–420
See application file for complete search history.

(56) References Cited

U.S. PATENT DOCUMENTS

| | | | | |
|---|---|---|---|---|
| 5,037,527 A | * | 8/1991 | Hayashi et al. | 204/403.12 |
| 5,234,568 A | * | 8/1993 | Tomita | 204/416 |

(Continued)

FOREIGN PATENT DOCUMENTS

| | | |
|---|---|---|
| EP | 0293858 A2 | 12/1988 |
| EP | 0450473 A2 | 10/1991 |

(Continued)

OTHER PUBLICATIONS

Extended European Search Report for Application No. 13187536.1—1559; dated Feb. 12, 2014.

*Primary Examiner* — J. Christopher Ball
(74) *Attorney, Agent, or Firm* — Cantor Colburn LLP

(57) ABSTRACT

In order to provide a planar type multi-ion sensor which is easily thinned and has high measurement accuracy, a multi-ion sensor 1 adapted to measure a concentration ratio of sodium ions to potassium ions in a sample solution, includes: a sodium ion electrode 41 selectively reacting to the sodium ions; a potassium ion electrode 42 selectively reacting to the potassium ions; and a common electrode 28 in contrast with the sodium ion electrode 41 and the potassium ion electrode 42, wherein the sodium ion electrode 41, potassium ion electrode 42 and common electrode 28 are provided on the same support body, the common electrode 28 does not include internal solution, and the concentration ratio of the sodium ions to the potassium ions is measured based on a variable A that is obtained by the following Equation (1),

FIG. 7

$$A = \frac{E_{Na}}{Q \times \alpha_{Na}} - \frac{E_K}{Q \times \alpha_K}. \qquad (1)$$

8 Claims, 7 Drawing Sheets (56) References Cited

U.S. PATENT DOCUMENTS

2004/0211242 A1 10/2004 Holmuhamedov
2006/0025748 A1 2/2006 Ye
2009/0021263 A1 1/2009 Hsiung et al.

FOREIGN PATENT DOCUMENTS

| EP | 1484007 A1 | 12/2004 |
| JP | 63181749 A | 7/1988 |
| WO | 20041048960 A1 | 6/2004 |

* cited by examiner

MULTI-ION SENSOR

CROSS REFERENCE TO RELATED APPLICATIONS

The present invention claims priority under 35 U.S.C. §119 to Japanese Application No. 2012-226286 filed Oct. 11, 2012, the entire content of which is incorporated herein by reference.

TECHNICAL FIELD

The present invention relates to a multi-ion sensor for measuring a concentration ratio between sodium ions and potassium ions.

BACKGROUND ART

In a human body, intracellular and extracellular osmotic pressures are kept constant and an action of kidney is properly maintained by an ion balance between sodium and potassium. However, in our eating habits of frequently using processed foods today, there is a tendency of an intake amount of sodium being large and an intake amount of potassium being reduced. Therefore, it is effective for management of a health condition to measure a ratio of Na/K.

A multi-ion sensor capable measuring concentrations of sodium ions and potassium ions in such as beverage is known as shown in, for example, Patent Literature 1. However, in the multi-ion sensor described in Patent Literature 1, after a concentration of sodium ions and a concentration of potassium ions are separately measured, a concentration ratio of sodium ions to potassium ions is obtained based on these measurement values.

In this multi-ion sensor configured to obtain a concentration ratio of sodium ions to potassium ions based on these measurement values after a concentration of sodium ions and a concentration of potassium ions are separately measured, it is necessary to present a constant reference potential to each of a sodium ion electrode and potassium ion electrode. Therefore, internal solution is required for a reference electrode. Therefore, it has been conventionally difficult to reduce a thickness of a multi-ion sensor integrally provided with a reference electrode to be thinner.

CITATION LIST

Patent Literature

Patent Literature 1: JPA-Sho-63-181749

SUMMARY OF INVENTION

Technical Problem

Therefore, the present invention has been made intending to provide a planar type multi-ion sensor that is easily thinned and has high measurement accuracy.

Solution to Problem

That is, a multi-ion sensor according to the present invention is adapted to measure a concentration ratio of sodium ions to potassium ions in a sample solution, and this multi-ion sensor includes: a sodium ion electrode selectively reacting to the sodium ions; a potassium ion electrode selectively reacting to the potassium ions; and a common electrode in contrast with the sodium ion electrode and the potassium ion electrode, wherein the sodium ion electrode, potassium ion electrode and common electrode are provided on the same support body, the common electrode does not include internal solution, and the multi-ion sensor is configured so as to measure the concentration ratio of the sodium ions to the potassium ions based on a variable A that is obtained by the following Equation (1).

$$A = \frac{E_{Na}}{Q \times \alpha_{Na}} - \frac{E_K}{Q \times \alpha_K} \quad (1)$$

In Equation (1), $E_{Na}$ represents a potential of the sodium ion electrode, $E_K$ represents a potential of the potassium ion electrode, Q represents a Nernst coefficient, $\alpha_{Na}$ represents a sensitivity coefficient of the sodium ion electrode, and $\alpha_K$ represents a sensitivity coefficient of the potassium ion electrode.

In the case where Equation (1) is represented while including a potential $E_{com}$ of the common electrode, it is represented as the following Equation (1)'. However, since the potential of the common electrode is canceled, even if the potential of the common electrode is varied, it does not affect the measurement result of the concentration ratio between the sodium ions and the potassium ions.

$$A = \left( \frac{E_{Na}}{Q \times \alpha_{Na}} - E_{com} \right) - \left( \frac{E_K}{Q \times \alpha_K} - E_{com} \right) \quad (1)'$$

Therefore, according to the present invention, since the measurement result of the concentration ratio between the sodium ions and the potassium ions is not affected even if the potential of the common electrode is varied, the potential of the common electrode under measurement may be varied but not be constant. Thus, the internal solution for the common electrode is unnecessary and therefore the sensor can be easily thinned.

Further, since the concentration ratio between the sodium ions and the potassium ions is measured based on the potential difference between the sodium ions and the potassium ions using respective sensitivity coefficients of the sodium ion electrode and the potassium ion electrode, even though these sensitivity coefficients are varied, the concentration ratio between the sodium ions and the potassium ions can be accurately measured.

The sensitivity coefficients $\alpha_{Na}$ and $\alpha_K$ may be 1 or may be determined by calibration. In the case where the sensitivity coefficients $\alpha_{Na}$ and $\alpha_K$ are 1, "$Q \times \alpha_{Na}$," and "$Q \times \alpha_K$" become Nernst coefficient Q represented by the following equation, and this becomes a theoretical slope which is 59.16 mV at a temperature of 25° C.

$$Q = \frac{2.303\, RT}{F}$$

Meanwhile, in the case where the sensitivity coefficients $\alpha_{Na}$ and $\alpha_K$ are determined by calibration, "$Q \times \alpha_{Na}$" and "$Q \times \alpha_K$" become practical slopes to be described later.

In addition, when a solution such as a drink containing sodium chloride is measured using Ag/AgCl containing chloride ions as the common electrode, it can be assumed in some cases that a chloride ion concentration is equal to a sodium ion concentration in quantity. In this case, the reference potential $E_0$ can be obtained by reducing the potential difference between the potential $E_{Cl}$ of the common electrode and the potential $E_{Na}$ of the sodium ion electrode to be half.

$$E_0 = \frac{E_{Na} - E_{Cl}}{2}$$

Therefore, the concentration of sodium ions can be obtained from Equation (2) using this reference potential.

$$C_{Na} = 10^{\wedge}\left(\frac{(E_{Na} - E_{Cl})}{2} \times \frac{F}{2.303\ RT} + \log C_{0Na}\right) \quad (2)$$

The concentration of the potassium ions can be obtained from Equation (3) using the concentration of the sodium ions obtained from Equation (2) and the concentration ratio between the sodium ions and the potassium ions measured based on the variable A obtained by Equation (1).

$$C_K = \frac{C_{oK}}{10^{\wedge}(A) \times C_{0Na}} \times C_{Na} \quad (3)$$

In Equations (2) and (3), A represents a value obtained by Equation (1), $E_{Cl}$ represents a potential of the common electrode, $C_{Na}$ represents the concentration of the sodium ions, $C_K$ represents the concentration of the potassium ions, $C_{0Na}$ represents the concentration of the sodium ions subjected to zero calibration, $C_{0K}$ represents the concentration of the potassium ions subjected to zero calibration, F represents a Faraday constant, R represents a gas constant, and T represents a temperature.

Therefore, in the multi-ion sensor according to the present invention, assuming that the sensitivity coefficients $\alpha_{Na}$ and $\alpha_K$ are 1 while using Ag/AgCl as the common electrode, the concentrations of the sodium ions and potassium ions can be calculated.

Advantageous Effects of Invention

Thus, according to the present invention, there can be obtained a planar type multi-ion sensor which can be easily thinned and has high measurement accuracy.

DETAILED DESCRIPTION OF PREFERRED EMBODIMENT

The following describes a first embodiment of the present invention referring to the accompanying drawings.

Figure 1:
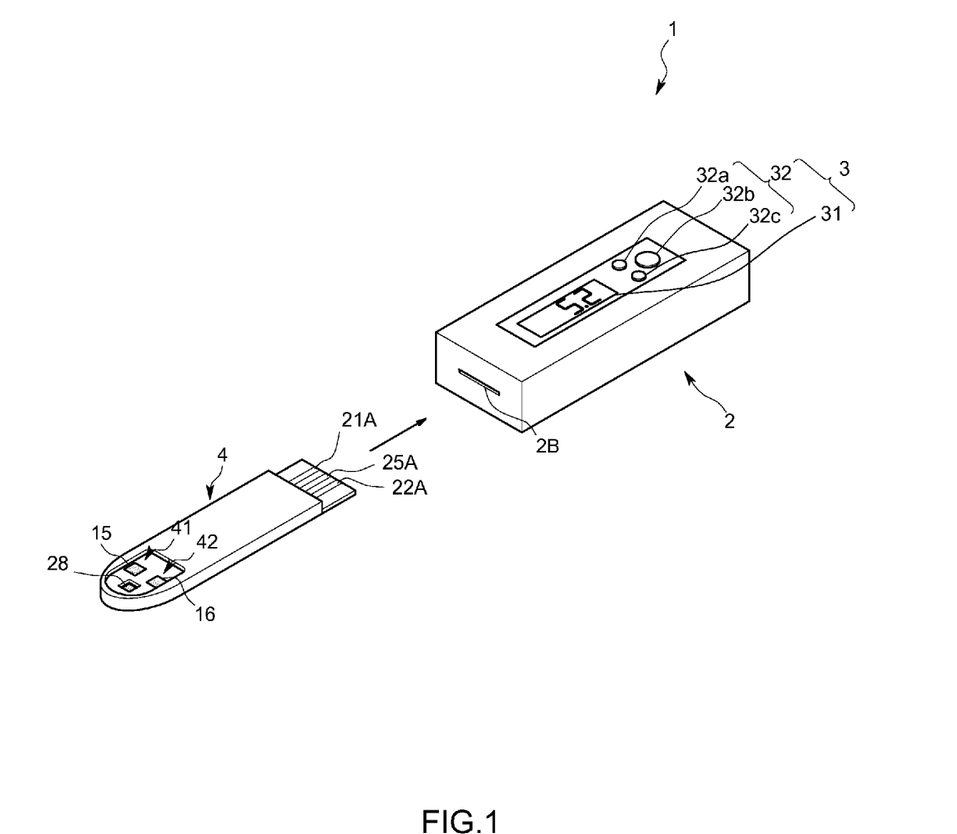
FIG. 1 is an overall schematic view of a multi-ion sensor according to a first embodiment of the present invention.
Figure 2:
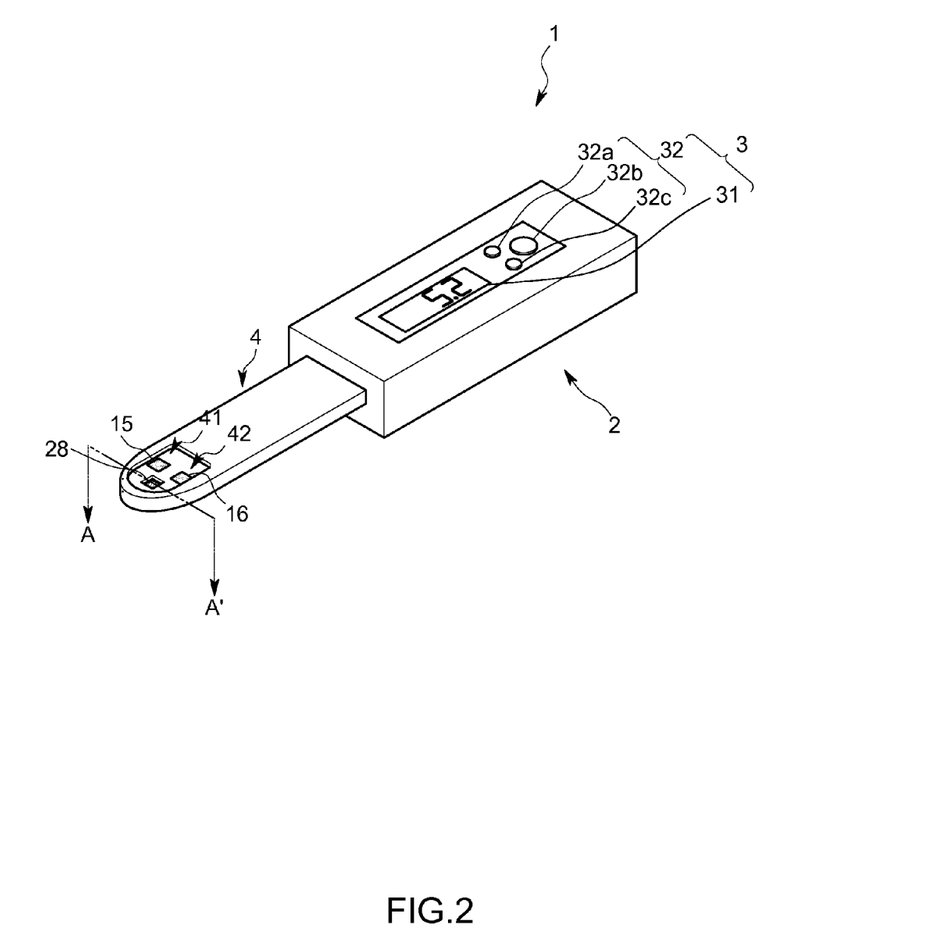
FIG. 2 is an overall schematic view of the multi-ion sensor according to the same embodiment.

A multi-ion sensor 1 according to the first embodiment is composite typed one including liquid membrane type ion-selective electrodes for measuring a concentration ratio of sodium ions to potassium ions in a sample solution and a common electrode integrated therewith. As shown in FIGS. 1 and 2, the multi-ion sensor 1 is comprised of a main body 2 made of synthetic resin, a display/operation part 3 formed on an upper surface of the main body 2 and a planar sensor 4 provided on a distal end side of the main body 2.

An arithmetic processing unit such as a microcomputer and a power supply part (either not shown) are incorporated in the main body 2. An insertion opening 2B is formed in a distal end surface of the main body 2 in order for inserting lead portions 21A, 22A and 25A of the planar sensor 4, and by inserting the lead portions 21A, 22A and 25A of the planar sensor 4 into the insertion opening 2B, the lead portions 21A, 22A and 25A are connected to a circuit board constituting the arithmetic processing unit incorporated in the main body 2.

The display/operation part 3 is comprised of a display unit 31 and an operation part 32 including various kinds of operation buttons such as a power button 32a, a calibration button 32b and a hold button 32c.

Figure 3:
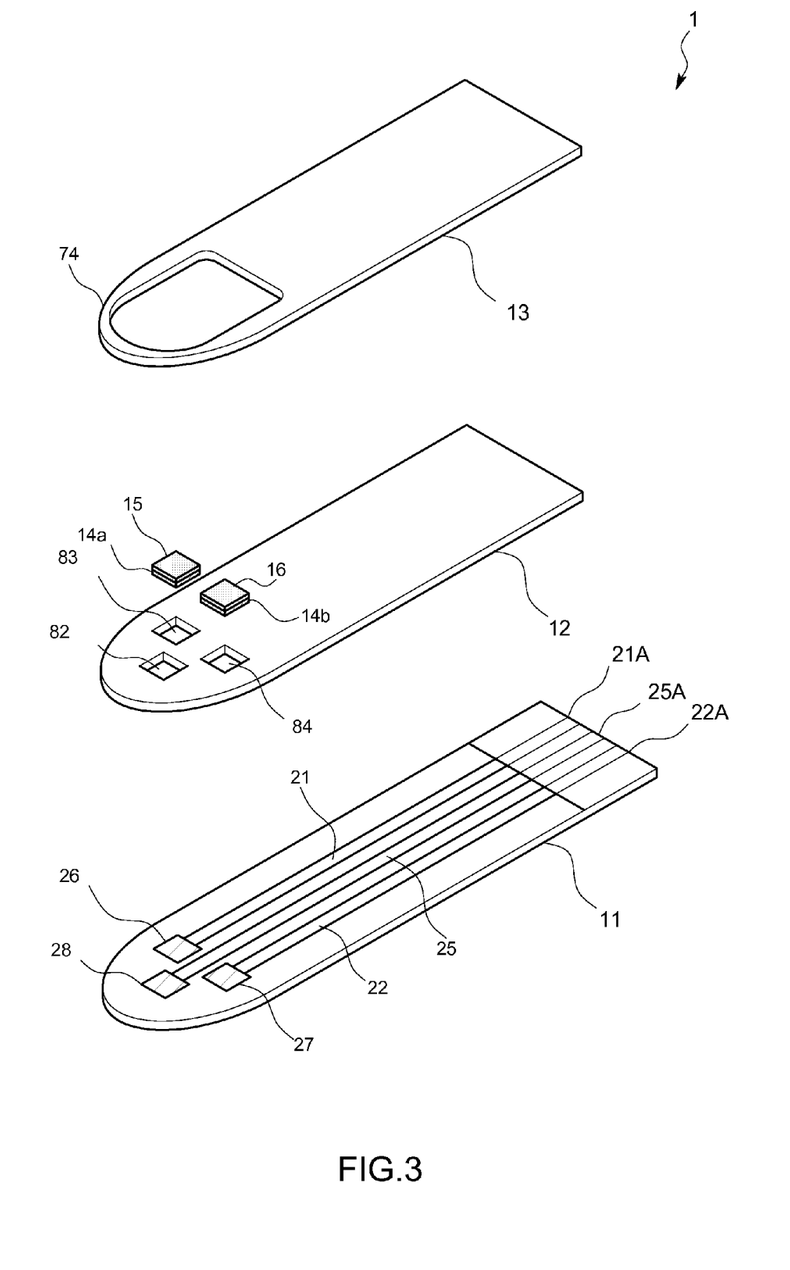
FIG. 3 is an exploded perspective view showing a planar sensor in the same embodiment.

The planar sensor 4 is configured so as to be integrally connected with the main body 2 by inserting the lead portions 21A, 22A and 25A into the insertion opening 2B or to be detachable from the main body 2. As shown in FIG. 3, the planar sensor 4 is made of a material having electrically insulating properties such as, for example, polyethylene terephthalate (referred to as "PET" hereinafter) and includes first to third substrates 11, 12 and 13 which are mutually laminated. Each of the substrates 11, 12 and 13 has a thickness in a degree of 300 μm and each distal end portion thereof is formed to be arcuate. Further, a test solution holder 74 is formed at a distal end of the third substrate 13 so as to surround a periphery of the second substrate 12.

On the first substrate 11, conductive parts 21, 22 and 25 are formed by performing, for example, a silk-screen printing of an Ag paste and the like after performing a predetermined pretreatment on the upper surface thereof. Resist processing of the conductive parts 21, 22 and 25 is performed except for the distal end portions thereof, and the distal end portions thereof are processed as follows. That is, the distal end portion of one outer side conductive part 21 is coated with AgCl to thereby form an internal electrode 26 of a $Na^+$ electrode 41 and the distal end portion of the other outer side conductive part 22 is also coated with AgCl to thereby form an internal electrode 27 of a $K^+$ electrode 42. Also, the distal end portion of the inner side conductive part 25 is coated with AgCl to thereby form a common electrode 28. Then, the rear end portions of the conductive parts 21, 22 and 25 respectively constitutes the lead portions 21A, 22A and 25A as they are.

Figure 6:
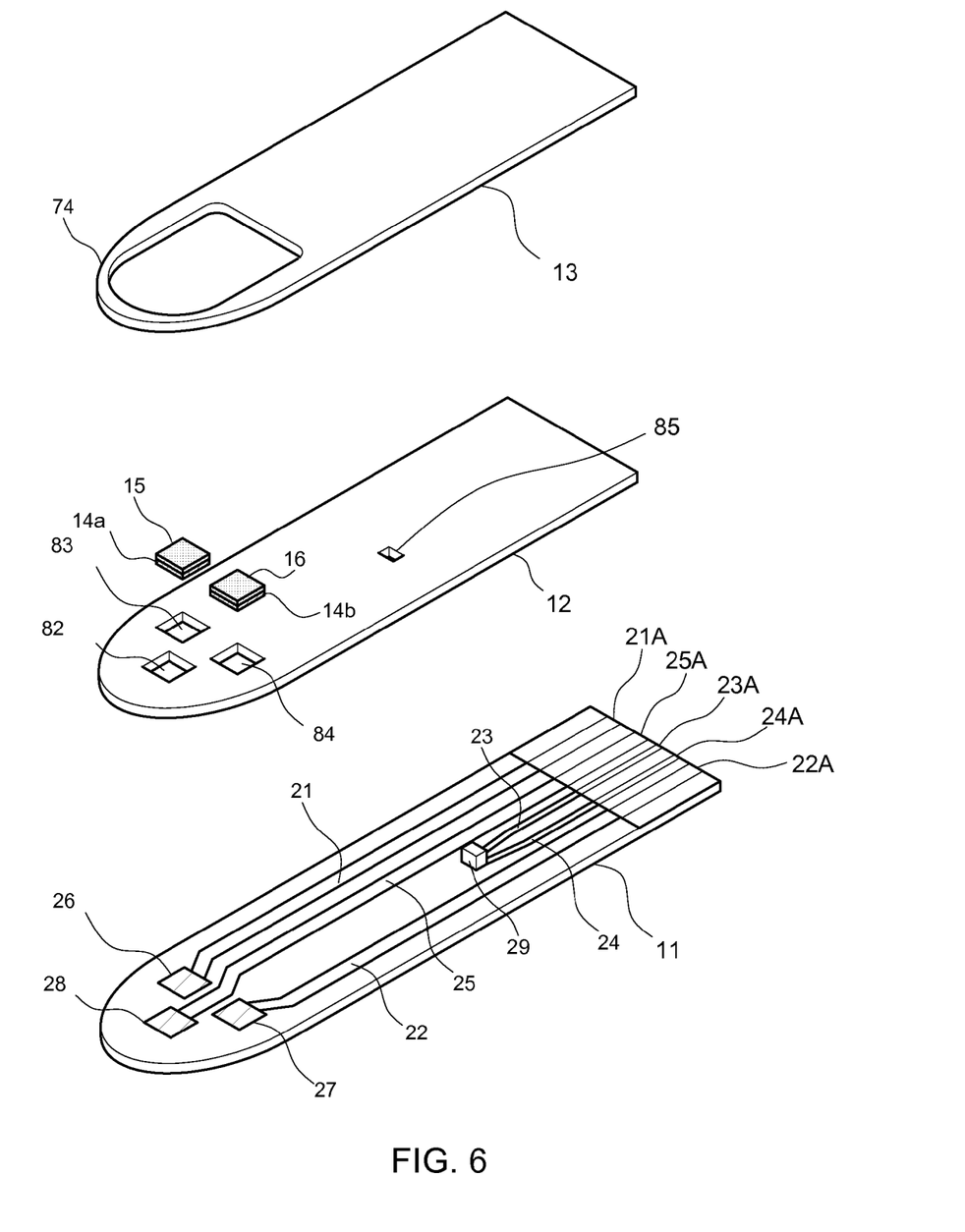
FIG. 6 is an exploded perspective view showing a planar sensor in another embodiment.

Further, as shown in FIG. 6, there may be provided a temperature compensation element 29 such as a thermistor on the first substrate 11. In FIG. 6, reference numerals 23 and 24 denote conductive parts which are connected to the temperature compensation element 29, reference numerals 23A and 24A denote lead portions configured of the rear end portions of the conductive parts 23 and 24, and reference numeral 85 denotes a rectangular through hole formed at a position in the second substrate 12 corresponding to the temperature compensation element 29, wherein the through hole 85 has a size substantially the same as the temperature compensation element 29. As shown in FIG. 3, in the case where there is not provided a temperature compensation element such as a thermistor, a constant (for example, 25° C. (=298.15K)) is used as T for calculating the Nernst coefficient Q.

In the second substrate 12, there are provided through holes 83 and 84 formed at positions corresponding to the internal electrodes 26 and 27, respectively, so as to have substantially the same shapes as those of the internal electrodes 26 and 27, and further there is provided a through hole 82 formed at a position corresponding to the common electrode 28 so as to have substantially the same shape as that of the common electrode 28.

Figure 4:
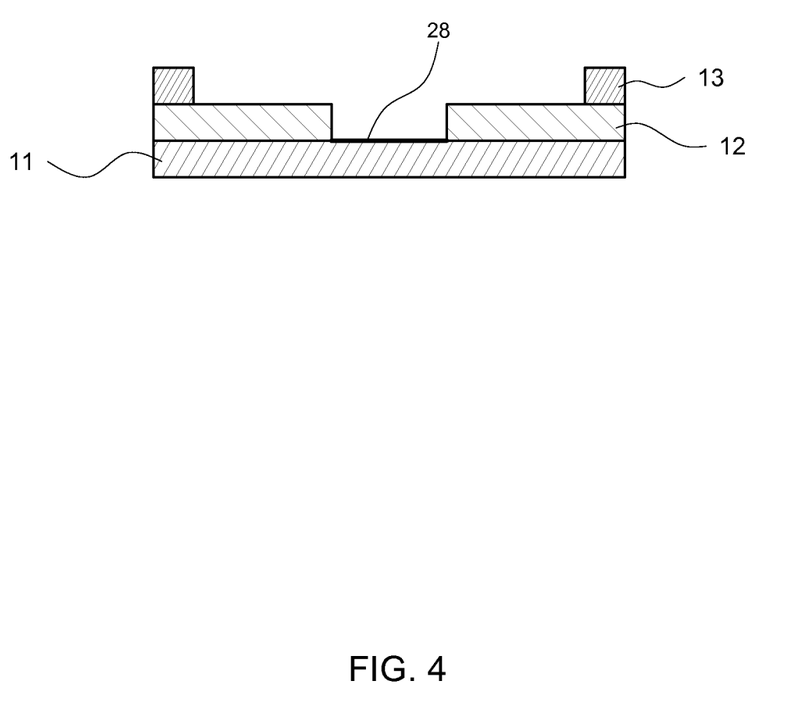
FIG. 4 is a cross sectional view taken along a line A-A' in FIG. 2.

Gel internal solutions 14a and 14b are respectively filled in the through holes 83 and 84 formed in the second substrate 12. The gel internal solution 14a is obtained in a process of, firstly making an internal solution added with NaCl, subsequently further adding agar as a gelling agent and glycerin as a gel evaporation inhibitor to the internal solution, and then curing the resultant internal solution. Similarly, the gel internal solution 14b is obtained in a process of, firstly making an internal solution added with KCl, subsequently further adding agar as a gelling agent and glycerin as a gel evaporation inhibitor to the internal solution, and then curing the resultant internal solution. Moreover, in order to adjust chloride ion concentrations of the gel internal solutions 14a and 14b, $CaCl_2$ may be further added. In addition, the chloride ion concentration of the internal solution may be adjusted to be in a degree of 0.05 to 1 M and may be combined with a chloride ion concentration of a sample and also may be combined with a chloride ion concentration of a calibration solution. However, in the case where $CaCl_2$ is not added, the chloride ion concentration of the internal solution is adjusted to be in a degree of 0.1 M. In particular, in the case where the chloride ion concentration of the internal solution is combined with a chloride ion concentration of a calibration solution, since the calibration solution may be used as a preservative solution, the chloride ion concentration of the internal solution may be stabilized for a long term and it is also possible to immediately perform a calibration. Meanwhile, as shown in FIG. 4, gel internal solution is not filled in the through hole 82 formed in the second substrate 12.

A sodium ion sensitive membrane 15 and potassium ion sensitive membrane 16 are further mounted on the gel internal solutions 14a and 14b in the through holes 83 and 84, respectively, formed in the second substrate 12 so as to be in contact with the gel internal solutions 14a and 14b and fixed to be substantially coplanar with the upper surface of the second substrate 12.

The sodium ion sensitive membrane 15 is obtained in a process of: adding a plasticizer and sodium ionophore to polyvinyl chloride (PVC) and then dissolving the same with an organic solvent such as tetrahydrofuran (referred to as "THF" hereinafter), then filling the resultant solution into the through hole 83 by such as a potting or inkjet printing method, and thereafter evaporating the organic solvent by heating to thereby form a solid state sodium ion sensitive membrane 15.

The potassium ion sensitive membrane 16 is formed in the same manner as the sodium ion sensitive membrane 15, except for using potassium ionophore.

Figure 5:
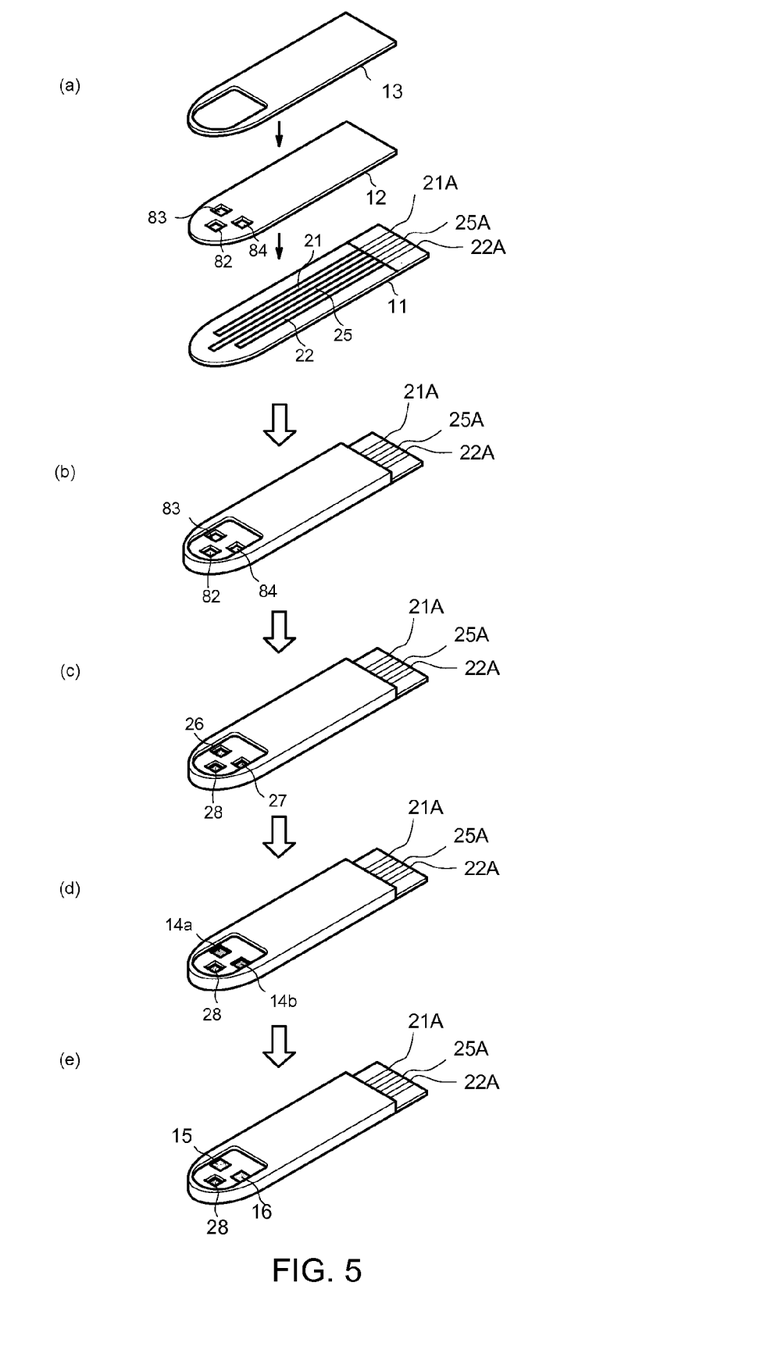
FIG. 5 is a schematic view showing a manufacturing process of a multi-ion sensor according to the same embodiment.

FIG. 5 shows a manufacturing procedure of the planar sensor 4 having such a configuration. First, the first substrate 11 having the conductive parts 21, 22 and 25 formed thereon, second substrates 12 and third substrate 13 are laminated via an adhesive (see FIG. 5(a)) to obtain a laminated body. The obtained laminated body is subjected to such as a roller and firmly bonded (see FIG. 5(b)). Next, AgCl is formed at a distal end portion of each of the conductive parts 21, 22 and 25 by such as a dipping method through the through holes 82, 83 and 84 provided in the second substrate 12, thereby forming the common electrode 28, internal electrode 26 of the $Na^+$ electrode 41 and internal electrode 27 of the $K^+$ electrode 42 (see FIG. 5(c)). Further, the gel internal solutions 14a and 14b are filled in the through holes 83 and 84 (see FIG. 5(d)), and then the sodium ion sensitive membrane 15 and potassium ion sensitive membrane 16 are mounted on the gel internal solutions 14a and 14b in the through holes 83 and 84, respectively (see FIG. 5(e)). At this time, THF is contained in the composition for the sodium ion sensitive membrane 15 and potassium ion sensitive membrane 16 and this THF dissolves the PET and the like composing the second substrate 12, whereby the sodium ion sensitive membrane 15 and potassium ion sensitive membrane 16 and the second substrate 12 are firmly fixed.

In order to measure a concentration ratio of sodium ions to potassium ions in a sample solution using the multi-ion sensor 1, first, drops of an appropriate amount of the sample solution is applied onto the common electrode 28, sodium ion sensitive membrane 15 and potassium ion sensitive membrane 16. Then, in the sodium ion sensitive membrane 15 and potassium ion sensitive membrane 16, there are generated electromotive forces corresponding to differences of the ion concentrations between the gel internal solutions 14a, 14b and the sample solution, respectively. These electromotive forces are detected as potential differences (voltages) of the internal electrode 26 of the $Na^+$ electrode 41, internal electrode 27 of the $K^+$ electrode 42 and the common electrode 28 to thereby calculate ratios between these potential differences and respective practical slopes (potential differences/concentrations). The practical slope is obtained by independently calibrating the $Na^+$ electrode 41 and $K^+$ electrode 42, respectively, using the same calibration solution for zero calibration as well as span calibration of a chloride ion concentration containing sodium ions, potassium ions, calcium chloride as an ionic strength adjustor, and the like. Internal solution is usually needed also for the common electrode in order to obtain a reference potential. However, in the present embodiment, by making activities of chloride ions of the calibration solutions for the zero calibration and span calibration to be equal, it is allowed to obtain the practical slope even without the internal solution. Moreover, in the case of using such as a platinum electrode or carbon electrode, since these electrodes respond to also redox substance such as dissolved oxygen, the calibration using a standard solution takes too much time until the potential is stabilized and it is not practical. However, in the present embodiment, by using a silver halide electrode such as an Ag/AgCl electrode having good compatibility with such as drinks containing sodium and potassium like sports drinks as the common electrode, it is made possible to perform a calibration also using a standard solution. One example of the calibration solution for the zero calibration and span calibration is shown in Table 1 as following.

TABLE 1

| | | Concentration (M) |
|---|---|---|
| Zero Calibration Solution | $C_{ONa}$ | 0.1 |
| | $C_{OK}$ | 0.02 |
| Span Calibration Soluiton | $C_{spanNa}$ | 0.03 |
| | $C_{spanK}$ | 0.01 |

Then, according to in the following Equation (4), the concentration ratio of sodium ions to potassium ions ($C_{Na}/C_K$) is calculated in the arithmetic processing unit to be displayed in the display unit 31.

$$C_{Na}/C_K = (10^{\wedge}((E_{Na}/SlopeNa^+) - \qquad (4)$$
$$(E_K/SlopeK^+))) \times (C_{0Na}/C_{0K})$$
$$= (10^{\wedge}(A)) \times (C_{0Na}/C_{0K})$$

Each parameter in Equation (4) is as follows.
$E_{Na}$: Potential of Na⁺ electrode 41
SlopeNa⁺: Practical slope of Na⁺ electrode 41
$E_K$: Potential of K⁺ electrode 42
SlopeK⁺: Practical slope of K⁺ electrode 42
In addition, the practical slopes "SlopeNa⁺ (=Q×$\alpha_{Na}$)" and "SlopeK⁺ (=Q×$\alpha_K$)" are derived from in the following Equations (5) and (6).

$$E_{spanNa} - E_{com} = Q \times \alpha_{Na} \times \log\left(\frac{C_{spanNa}}{C_{0Na}}\right) \qquad (5)$$

$$E_{spanK} - E_{com} = Q \times \alpha_K \times \log\left(\frac{C_{spanK}}{C_{0K}}\right) \qquad (6)$$

Each parameter in Equations (5) and (6) is as follows.
$E_{spanNa}$: Potential of Na⁺ electrode 41 at a time of span calibration
$E_{spanK}$: Potential of K⁺ electrode 42 at a time of span calibration
$E_{com}$: Potential of common electrode 28

In the multi-ion sensor 1 according to the present embodiment, in order to obtain the practical slope, the chloride ion concentrations of the calibration solutions for the zero calibration and span calibration are made constant. Thus, the sensitivity of each of the sensors of the Na⁺ electrode 41 and K⁺ electrode 42 can be obtained based on the potential difference between each of the Na⁺ electrode 41 and K⁺ electrode 42 and the common electrode 28 composed of an Ag/AgCl electrode.

Here, in the case of measuring a solution containing sodium chloride as a measurement sample while using the Ag/AgCl electrode as the common electrode 28, in the case where the sodium ion concentration is substantially equal to the sodium ion concentration in amount, the reference potential can be obtained by rendering the potential difference between the common electrode 28 and the sodium ion electrode 41 to be half.

$$E_0 = \frac{E_{Na} - E_{Cl}}{2}$$

Each parameter in the above Equation is as follows.
$E_o$: Reference potential
$E_{Na}$: Potential of Na⁺ electrode 41
$E_{Cl}$: Potential of common electrode 28
If the reference potential is obtained, the sodium ion concentration can be obtained from Equation (2) as follows.

$$C_{Na} = 10^{\wedge}\left(\frac{(E_{Na} - E_{Cl})}{2} \times \frac{F}{2.303\,RT} + \log C_{0Na}\right) \qquad (2)$$

Thus, if the sodium ion concentration is obtained, the potassium ion concentration can be measured by in the following Equation (3) which is obtained by modifying Equation (4) mentioned above for calculating a concentration ratio between the sodium ion concentration and the potassium ion concentration. Note that, in the following Equation (3), it is assumed that sensitivity coefficients $\alpha_{Na}$ and $\alpha_K$ in obtaining A are 1.

$$C_K = \frac{C_{oK}}{10^{\wedge}(A) \times C_{0Na}} \times C_{Na} \qquad (3)$$

Note that each parameter in the above Equations (2) and (3) is as follows.
A: Variable obtained by Equation (1)
F: Faraday constant
R: Gas constant
T: Temperature In the multi-ion sensor 1 according to the present embodiment configured as described above, even though the potential of the common electrode 28 is varied, the variation does not affect the measurement result of the concentration ration between the sodium ions and the potassium ions. Therefore, the potential of the common electrode 28 may be varied but not be constant. Therefore, since the internal solution is not required for the common electrode 28, the sensor 1 can be easily reduced in thickness.

In addition, since the concentration ration between the sodium ions and the potassium ions is measured using the respective practical slopes of the Na⁺ electrode 41 and K⁺ electrode 42, even though these slopes are varied, the concentration ration between the sodium ions and the potassium ions can be measured accurately.

Furthermore, since the Ag/AgCl electrode is used as the common electrode 28, the variation in potential is small even without internal solution and it is possible to deal with also sodium ions and potassium ions of having the concentrations largely changed in the sample solution. In addition, as the common electrode 28, an Ag/AgBr electrode or Ag/AgI electrode can be also used other than the Ag/AgCl electrode.

In addition, in the case where the Ag/AgCl electrode is used as the common electrode 28, the sodium ion concentration and potassium ion concentration can be calculated.

Figure 7:
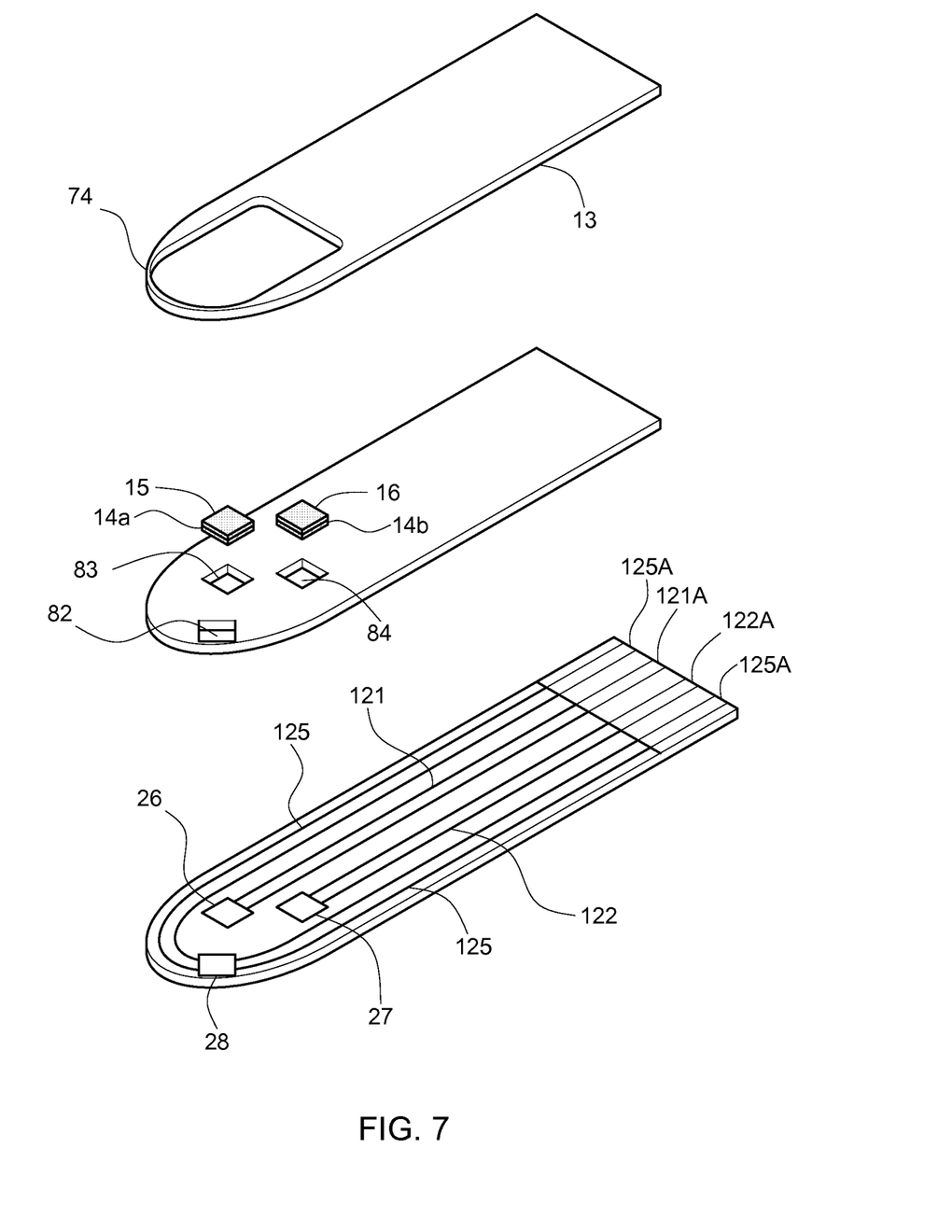
FIG. 7 is an exploded perspective view showing a planar sensor according to a second embodiment of the present invention.

Next, the following describes a second embodiment referring to an accompanying drawing of FIG. 7.

In the multi-ion sensor 1 according to the second embodiment, the configuration of the conductive part formed on the first substrate 11 is different from that of the first embodiment. Note that the same reference numerals are given to the same parts as the first embodiment and the explanations thereof are omitted here.

As shown in FIG. 7, conductive parts 121, 122 and 125 are formed on the first substrate 11 by performing, for example, a silk-screen printing of an Ag paste and the like so that the conductive part 125 surrounds the conductive parts 121 and 122. Distal end portions of the conductive parts 121 and 122 are coated with AgCl to thereby form internal electrodes 26 and 27 of the Na⁺ electrode 41 and K⁺ electrode 42, respectively. A partial portion of the conductive part 125 formed so as to surround the conductive parts 121 and 122 is coated with AgCl to form a common electrode 28. The conductive parts 121, 122 and 125 except for the portions where the electrodes are formed are subjected to resist processing. Then, the rear end portions of the conductive parts 121, 122 and 125 constitute lead portions 121A, 122A and 125A, respectively.

In the multi-ion sensor 1 according to the second embodiment configured as described above, since the conductive part 125 acts as an electrostatic shield, it is possible to prevent sensitivity of the sensor from being degraded. Further, since the electrostatic shield can be formed at the same time of forming the common electrode 28, it is not necessary to separately provide an electrostatic shield and the electrostatic shield can be easily formed.

Note that the present invention is not limited to the above embodiments.

Although the multi-ion sensor 1 according to the above embodiments is provided with the gel internal solutions 14a and 14b for the sodium ion sensitive membrane 15 and potassium ion sensitive membrane 16, a concentration ration of sodium ions to potassium ions can be calculated without the gel internal solutions 14a and 14b. Therefore, the gel internal solutions 14a and 14b may be omitted in order to reduce the thickness of the planar sensor 4 to be film-like shaped.

The planar sensor 4 may be disposable goods to be disposed after using the same, for example, 5 to 10 times. In this case, a practical slope obtained in advance has been previously written in a memory chip embedded in the main body 2 or the planar sensor 4 of the multi-ion sensor 1, and thus a user may perform only a zero calibration so that the variable A in the Equation (3) becomes 0 mV. At this time, for example, a gelled zero calibration solution may be previously pasted on a surface where the electrodes of the planar sensor 4 are formed, whereby the zero calibration may be carried out by removing the zero calibration solution.

Regarding each of the Equations (1) to (6), an equivalent expression that is deformed or the like may be used and the variable A may be not only a raw value as it is but also may be added with coefficients and the like.

In addition, the embodiments and modified embodiment described above may be partly or entirely combined appropriately and various modifications are of course possible within the scope unless departing from the intended spirit thereof.

EXAMPLE

The following describes the present invention in more detail by exemplifications, but the present invention is not intended to be limited to these examples.

In order to verify the reliability of the multi-ion sensor according to the present invention, the following tests were performed.

<Test>

First, as a practice test solution, there were prepared a solution of a known concentration ratio of sodium ions to potassium ions. In this example, the solution of a sodium ion concentration being 0.2 mol/dm³ and potassium ion concentration being 0.05 mol/dm³ were prepared. As to this test solution, the concentration ratio of sodium ions to potassium ions was measured using the multi-ion sensor of the present invention. The measurement results thereof are shown in Table 2.

TABLE 2

| | |
|---|---|
| $C_{Na}$ | 0.2 Mol/dm3 |
| $C_K$ | 0.05 Mol/dm3 |
| $C_{0Na}$ | 0.15 Mol/dm3 |
| $C_{0K}$ | 0.03 Mol/dm3 |
| $E_{Na}$ | 17.7 mV |
| $E_K$ | 22.9 mV |
| $E_{Na} - E_K$ | −5.2 mV |
| SlopeNa⁺ | 57 mV/dec |
| SlopeK⁺ | 57 mV/dec |
| $C_{Na}/C_K$ | 4.1 |

The concentration ratio of sodium ions to potassium ions measured by the multi-ion sensor of the present invention using the values listed in Table 2 was 4.1. Since the concentration ratio of sodium ions to potassium ions of the practice test solution is 4.0, it is understood that the concentration ratio of sodium ions to potassium ions measured by the multi-ion sensor of the present invention can be an accurate value almost equal to the measured value.

REFERENCE SIGNS LIST

1 . . . Multi-ion sensor
15 . . . Sodium ion-sensitive membrane
16 . . . Potassium ion-sensitive membrane
28 . . . Common electrode
41 . . . Na⁺ electrode
42 . . . K⁺ electrode

The invention claimed is:

1. A multi-ion sensor adapted to measure a concentration ratio of sodium ions to potassium ions in a sample solution, comprising:
 a sodium ion electrode selectively reacting to the sodium ions;
 a potassium ion electrode selectively reacting to the potassium ions;
 a common electrode that is a reference electrode common to both the sodium ion electrode and the potassium ion electrode, and
 an microcomputer, wherein
 the sodium ion electrode, the potassium ion electrode, and the common electrode are provided on same support body,
 the common electrode does not include internal solution, and
 the microcomputer is structured to calculate the concentration ratio of the sodium ions to the potassium ions using a potential measured by the sodium ion electrode and a potential measured by the potassium ion electrode based on a variable A that is obtained by the following Equation (1), $$A = \frac{E_{Na}}{Q \times \alpha_{Na}} - \frac{E_K}{Q \times \alpha_K} \quad (1)$$

in Equation (1), $E_{Na}$ represents a potential of the sodium ion electrode, $E_K$ represents a potential of the potassium ion electrode, Q represents a Nernst coefficient, $\alpha_{Na}$ represents a sensitivity coefficient of the sodium ion electrode, and $\alpha_K$ represents a sensitivity coefficient of the potassium ion electrode.

2. The multi-ion sensor according to claim 1, wherein the sensitivity coefficients $\alpha_{Na}$ and $\alpha_K$ are 1.

3. The multi-ion sensor according to claim 1, wherein the sensitivity coefficients $\alpha_{Na}$ and $\alpha_K$ are coefficients determined by calibration.

4. The multi-ion sensor according to claim 1, wherein an Ag/AgCl electrode is used as the common electrode,
 the sensitivity coefficients $\alpha_{Na}$ and $\alpha_K$ are 1, and
 the microcomputer is structured to measure the concentration of the sodium ions by the following Equation (2) and measure the concentration of the potassium ions by the following Equation (3), $$C_{Na} = 10^{\wedge}\left(\frac{(E_{Na} - E_{Cl})}{2} \times \frac{F}{2.303\ RT} + \log C_{0Na}\right) \quad (2)$$

$$C_K = \frac{C_{oK}}{10^{\wedge}(A) \times C_{0Na}} \times C_{Na} \quad (3)$$

in Equations (2) and (3), A is a value obtained by Equation (1), $E_{Cl}$ represents a potential of the common electrode, $C_{Na}$ represents the concentration of the sodium ions, $C_K$ represents the concentration of the potassium ions, $C_{0Na}$ represents the concentration of the sodium ions subjected to zero calibration, $C_{0K}$ represents the concentration of the potassium ions subjected to zero calibration, F represents a Faraday constant, R represents a gas constant, and T represents a temperature.

5. A method of calculating a concentration ratio of sodium ions to potassium ions in a sample solution, comprising:
providing a multi-ion sensor comprising:
a sodium ion electrode selectively reacting to the sodium ions;
a potassium ion electrode selectively reacting to the potassium ions;
a common reference electrode that is common to both the sodium ion electrode and the potassium ion electrode, and
an arithmetic processing unit, wherein the sodium ion electrode, the potassium ion electrode, and the common electrode are provided on same support body, the common electrode does not include internal solution;
calculating the concentration ratio of the sodium ions to the potassium ions based on a variable A that is obtained by the following Equation (1), $$A = \frac{E_{Na}}{Q \times \alpha_{Na}} - \frac{E_K}{Q \times \alpha_K} \quad (1)$$

wherein, in Equation (1), $E_{Na}$ represents a potential of the sodium ion electrode, $E_K$ represents a potential of the potassium ion electrode, Q represents a Nernst coefficient, $\alpha N_{Na}$ represents a sensitivity coefficient of the sodium ion electrode, and $\alpha_K$ represents a sensitivity coefficient of the potassium ion electrode.

6. The method of calculating a concentration ratio of sodium ions to potassium ions in a sample solution according to claim 5, wherein the sensitivity coefficients αNa and αK are 1.

7. The method of calculating a concentration ratio of sodium ions to potassium ions in a sample solution according to claim 5, wherein the sensitivity coefficients αNa and αK are coefficients determined by calibration.

8. The method of calculating a concentration ratio of sodium ions to potassium ions in a sample solution according to claim 5, wherein an Ag/AgCl electrode is used as the common electrode,
the sensitivity coefficients αNa and αK are 1, and
the arithmetic processing unit is structured to measure the concentration of the sodium ions by the following Equation (2) and measure the concentration of the potassium ions by the following Equation (3), $$C_{Na} = 10^{\wedge}\left(\frac{(E_{Na} - E_{Cl})}{2} \times \frac{F}{2.303\ RT} + \log C_{0Na}\right) \quad (2)$$

$$C_K = \frac{C_{oK}}{10^{\wedge}(A) \times C_{0Na}} \times C_{Na} \quad (3)$$

in Equations (2) and (3), A is a value obtained by Equation (1), ECl represents a potential of the common electrode, CNa represents the concentration of the sodium ions, CK represents the concentration of the potassium ions, C0Na represents the concentration of the sodium ions subjected to zero calibration, C0K represents the concentration of the potassium ions subjected to zero calibration, F represents a Faraday constant, R represents a gas constant, and T represents a temperature.

\* \* \* \* \*